United States Patent
Ikeda et al.

(10) Patent No.: US 7,039,162 B2
(45) Date of Patent: May 2, 2006

(54) X-RAY DIAGNOSIS APPARATUS

(75) Inventors: Shigeyuki Ikeda, Chiba (JP); Katsumi Suzuki, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 92 days.

(21) Appl. No.: 10/484,579

(22) PCT Filed: Jul. 23, 2002

(86) PCT No.: PCT/JP02/07437

§ 371 (c)(1), (2), (4) Date: Jan. 23, 2004

(87) PCT Pub. No.: WO03/009760

PCT Pub. Date: Feb. 6, 2003

(65) Prior Publication Data
US 2004/0174953 A1   Sep. 9, 2004

(30) Foreign Application Priority Data
Jul. 23, 2001   (JP) .............................. 2001-221414

(51) Int. Cl.
H05G 1/64   (2006.01)

(52) U.S. Cl. ................................. 378/98.8; 250/370.09

(58) Field of Classification Search ............... 378/98.8, 378/98.12, 19; 250/370.01–370.15; 348/294
See application file for complete search history.

(56) References Cited

U.S. PATENT DOCUMENTS

| 6,453,008 | B1 * | 9/2002 | Sakaguchi et al. | ......... 378/98.7 |
| 6,697,663 | B1 * | 2/2004 | Lin | ............................ 600/425 |

FOREIGN PATENT DOCUMENTS

| JP | 01-223880 | * | 9/1989 |
| JP | 05-292352 | * | 11/1993 |
| JP | 07-136154 | * | 5/1995 |

* cited by examiner

Primary Examiner—Craig E. Church
Assistant Examiner—Jurie Yun
(74) Attorney, Agent, or Firm—Antonelli, Terry, Stout and Kraus, LLP

(57) ABSTRACT

An X-ray diagnosis apparatus includes an X-ray tube for projecting X-rays onto a subject, a two-dimensional X-ray detector for detecting X-ray signals from the subject, an image processing unit for generating image signals to perform image display of an image represented by the X-ray signals received from the two-dimensional X-ray detector, and an image displaying unit for displaying the image. The X-ray diagnosis apparatus further has a noise eliminating unit for generating noise correction signals from the X-ray signal of two scanning lines that are adjacent to each other out of a plurality of scanning lines of the two-dimensional X-ray detector and for eliminating noise in an X-ray signal of the scan lines by using the noise correction signal.

24 Claims, 6 Drawing Sheets

US 7,039,162 B2

X-RAY DIAGNOSIS APPARATUS

TECHNICAL FIELD

The present invention relates to an X-ray diagnostic apparatus, and, more particularly, to a technique for reducing line correlation noise, which causes deterioration of the image quality in images obtained by a two-dimensional semiconductor X-ray detector (Flat Panel: FP).

BACKGROUND OF THE INVENTION

In a conventional X-ray diagnostic apparatus, as disclosed in Japanese Unexamined Patent Publication No. 2000-33083, "X-ray image forming apparatus", data for correction is calculated from the outputs of a detector derived from an area where X-ray beams do not impinge, which area is referred to as a dark area within the detection areas of a two-dimensional semiconductive X-ray detector, and data for correction of an area where X-ray beams do impinge (hereinafter referred to as the "effective area") are generated by using the data for correction calculated from the detector outputs derived from the dark area.

However, it has been found that noise might enter even in pixels disposed in the dark area. In this case, the data for correction generated in the dark area may be mixed with noise even when such noise is not mixed in the data obtained in the effective area. Therefore, there are problems in that the image data of one line may have an offset in gain relative to an adjacent line, to thereby generate line noise in a diagnostic image.

SUMMARY OF THE INVENTION

To solve the above-mentioned problem, the X-ray diagnostic apparatus according to the present invention includes: an X-ray tube for irradiating an object to be examined with X-rays; a two-dimensional X-ray detector for detecting X-ray signals from the object; image processing means for producing image signals which represent an image of the object based on the X-ray signals obtained from the two-dimensional X-ray detector; and image display means for displaying an image based on the image signals, the X-ray diagnostic apparatus further including noise eliminating means for producing a noise correction signal from two adjacent scan lines among a plurality of scan lines of the X-ray signals produced by the two-dimensional X-ray detector, and for eliminating a noise component in the X-ray signals of the scan lines by using the noise correction signal.

An object of the present invention is to provide an X-ray diagnostic apparatus that can reduce an effect of noise generated in calculating the data for correction from an output of a sensor obtained in its dark area.

BEST MODE FOR CARRYING OUT THE INVENTION

Hereinafter, the present invention will be described on the basis of the embodiments, with reference to the drawings.

Figure 1:
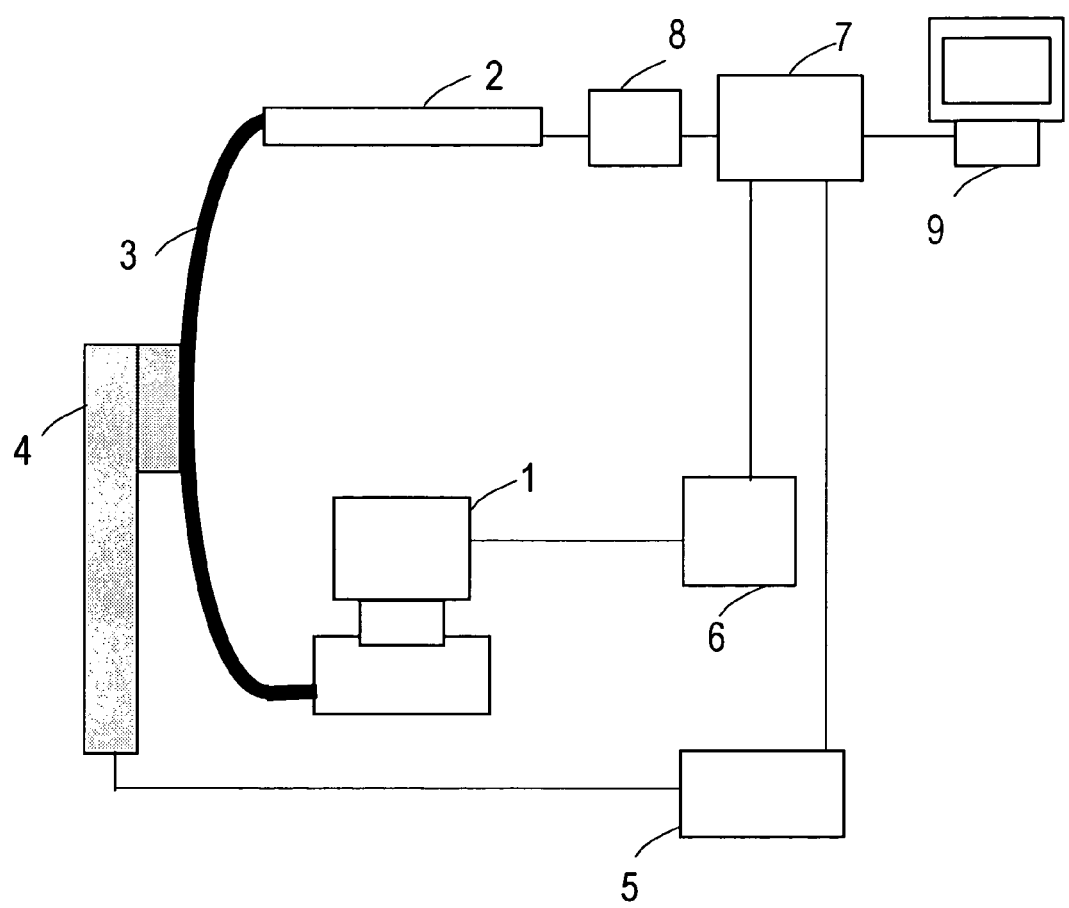
FIG. 1 is a block diagram of an X-ray diagnostic apparatus using a two-dimensional X-ray detector.

FIG. 1 shows the basic structure of an X-ray diagnostic apparatus, which includes an X-ray tube 1; a two-dimensional detector 2; a C-arm 3; a supporting device 4; a supporting device controller 5; a collimator controller 6; an image processing unit 7; a noise eliminating unit 8; and an image display unit 9. The X-ray tube 1 and the two-dimensional detector 2 are mounted on respective ends of the C-arm 3, which is supported by the supporting device 4. A collimator for limiting the X-ray radiation field is attached to the X-ray tube 1, and it is controlled by the collimator controller 6. The supporting device controller 5 controls the supporting device 4 so as to control the distance between the X-ray tube 1 and the two-dimensional detector 2, the rotation of the C-arm 3, and so on. The noise eliminating unit 8 eliminates noise in an output signal of the two-dimensional detector 2, and transfers these signals as image signals to the image processing unit 7. The image processing unit 7 processes the image signal, and displays the resulting image on the image display unit 9. The image processing unit 7 also operates to instruct the collimator controller 6 and the supporting device controller 5 to acquire an adaptive image.

Figure 5:
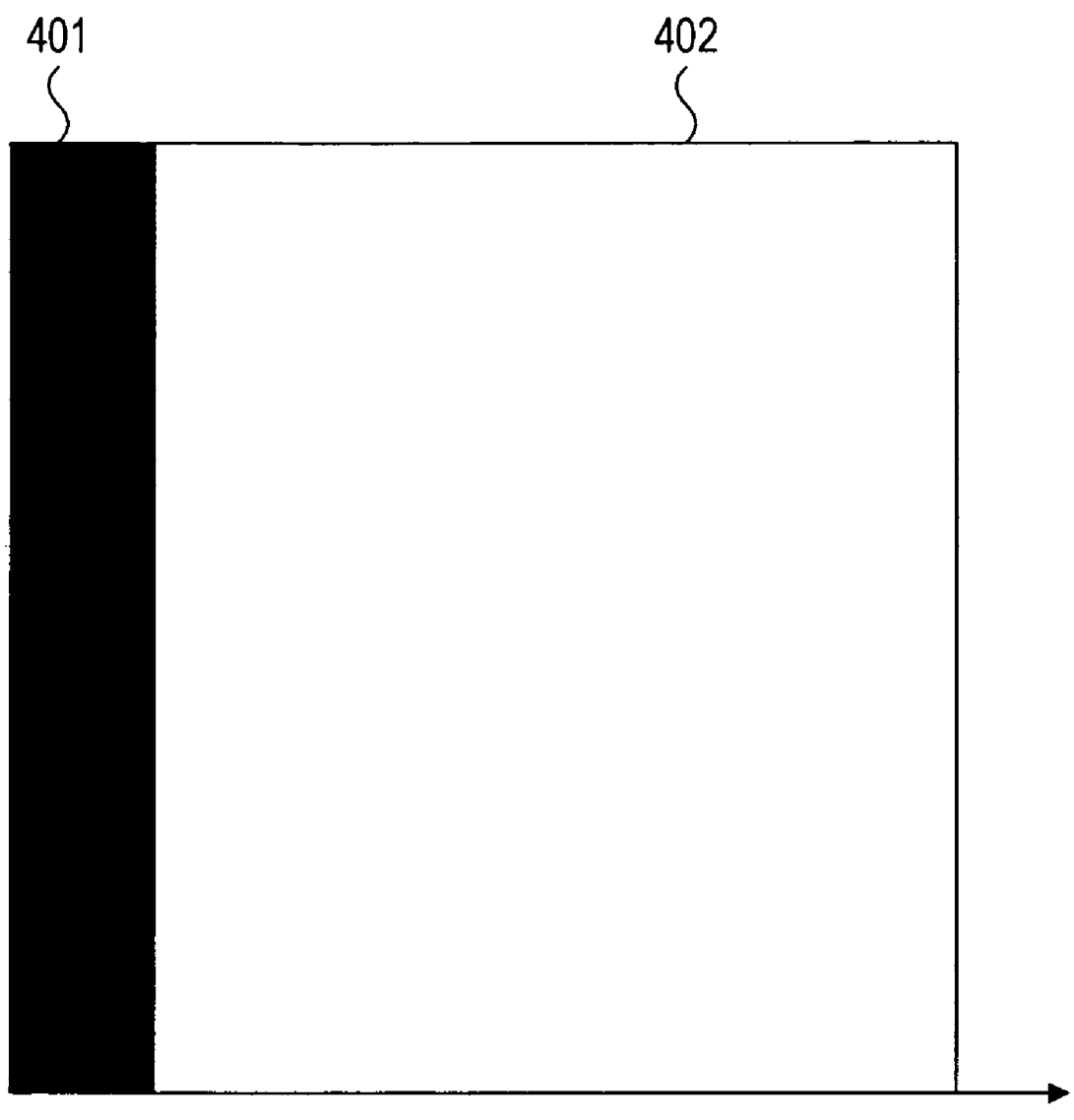
FIG. 5 is a diagram showing a detecting area of an X-ray image and a non-detecting area thereof within a total pixel area of a two-dimensional semiconductor X-ray detector.

FIG. 5 shows a detecting area of the X-ray image and a non-detecting area thereof within the total pixel area of the two-dimensional semiconductor X-ray detector, wherein reference numeral 401 represents the non-detecting area (dark area), and reference numeral 402 represents the detecting area (effective area). In accordance with the present invention, the basic operation includes, first, calculating an average value of sensor outputs in the dark area 401 at each scan line, and next, reducing the line noise by subtracting the data for correction, represented by the calculated average value, from an output of the sensor in the effective area 402.

Figure 6:
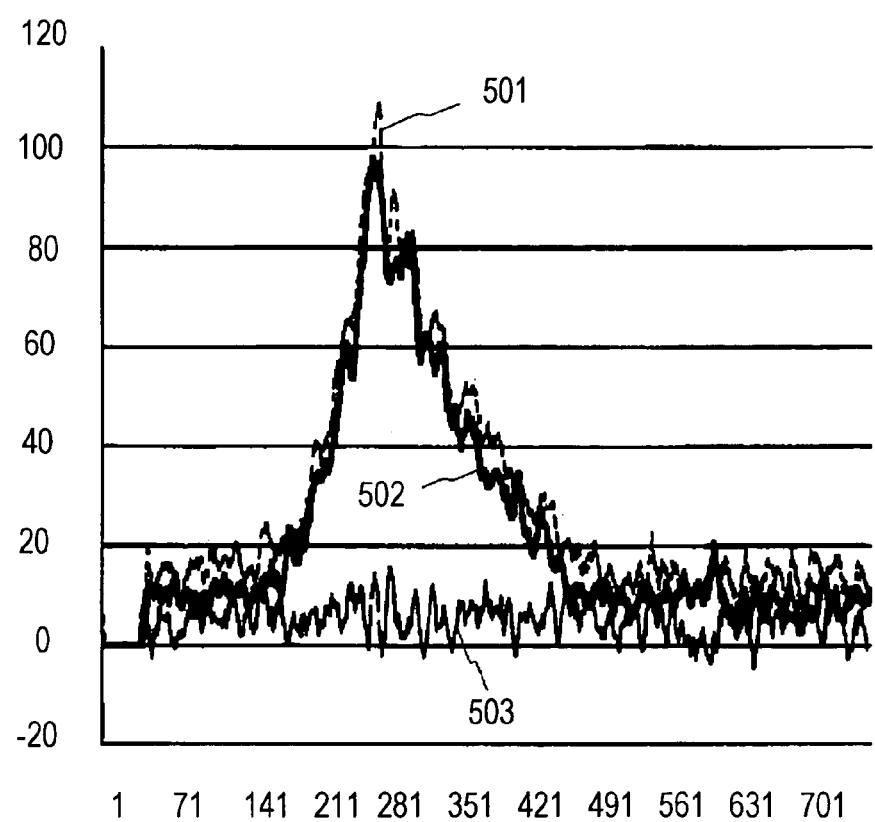
FIG. 6 is a graph of image data in a line where line noise is generated and a line adjacent to the line where the line noise is generated.

FIG. 6 is a graph of image data on a line where line noise is generated and on a line adjacent to the line where the noise is generated, wherein the ordinate indicates a pixel value, and the abscissa indicates an address in the line direction. Reference numeral 501 represents image data on the line where the line noise is generated, reference numeral 502 represents image data on the line adjacent to the line where the line noise is generated, and reference numeral 503 represents the difference between the image data of the line where the line noise is generated and that of the adjacent line.

First, when an organ receiving a substantially uniform X-ray dosage, like that of a human body, is subjected to radiography, it is generally rare that pixel values on adjoining lines in the X-ray image of the object greatly vary, because the correlation is held within an extremely minute area. Therefore, the value of image data on a predetermined line should be substantially the same as the value of image data on an adjoining line, whereby the difference between these adjoining lines becomes very small.

Therefore, according to the above-described method of reducing line noise, the average value of the sensor outputs in the dark area 401 is calculated at each line; this average value is used as the data for correction for each line; and the data for correction of each line is subtracted from the sensor output at the corresponding line in the effective area 402. Therefore, when a noise is mixed in the dark area, the data for correction on the line where the noise is mixed varies, and the sensor output to be acquired is affected by the noise. Accordingly, the difference 503 at each address, obtained by subtracting the image data 501 on the line where the noise is mixed in the dark area from the image data 502 on the line adjacent to the line where the noise is mixed, is close to the data for correction.

By comparing a difference between adjoining lines at each address (each pixel), it is possible to judge whether or not a line noise exists in the dark area. However, in comparing these values at each pixel, it is difficult to determine whether or not line noise exists. Accordingly, in accordance with the present invention, all the difference values of one line are summed up, and the existence of line noise in the dark area is judged from the sum of the difference values. When line noise is not mixed in the dark area, as described above, the difference value obtained between the data values on the line to be judged and a line adjacent thereto results in a very small value. Therefore, a summed-up value obtained by adding the difference values in an address direction also results in a small value. Particularly, on a line of an image without line noise generation, a negative difference value could be obtained depending on its address because of a correlation with an adjacent line, whereby the result of summing up the difference values obtained at each line is still smaller.

On the other hand, since the value of the image data on a line where noise is mixed in the dark area is increased by the amount corresponding to the mixed noise, as described above, the difference in value between a line mixed with noise and a line adjacent thereto is also increased by a value corresponding to the noise. Consequently, when the difference values of one line are added, a summed-up difference value is naturally increased by a value corresponding to the noise mixed in the dark area, whereby the summed-up value becomes close to an error of a correction value. Accordingly, when the error of the correction value is large, the summed-up value also becomes large. The number of pixels in the dark area 401 is generally 64 to 128. Meanwhile, according to the present invention, the sensor output in the dark area 401, i.e., the average value of the pixel values in the dark area 401, is utilized, as described above, whereby the error does not become large and the standard value of the error can be set, for example, at about 5 to 10 for one pixel. Accordingly, in a two-dimensional X-ray detector having 1024 pixels for one line, when the error per pixel is 5, the error is about: 1024×5=5120. Further, when the error per pixel is 10, the error value is about: 1024×10=10240.

Accordingly, when the result of adding the difference values of one line is between 5120 and 10240, it can be judged that noise is mixed in the dark area 401. In this case, according to the present invention, the acquired value between 5120 and 10240 is divided by the pixel number, and the thus obtained value is subtracted from every pixel value in the X-ray detection area 402, or added to every pixel value of the X-ray detection area 402, whereby the pixel values that have been corrected relative to the noise mixed in the dark area 401 is further corrected, wherein the same effect as modification of the corrected data is obtainable.

EMBODIMENT 1

Figure 2:
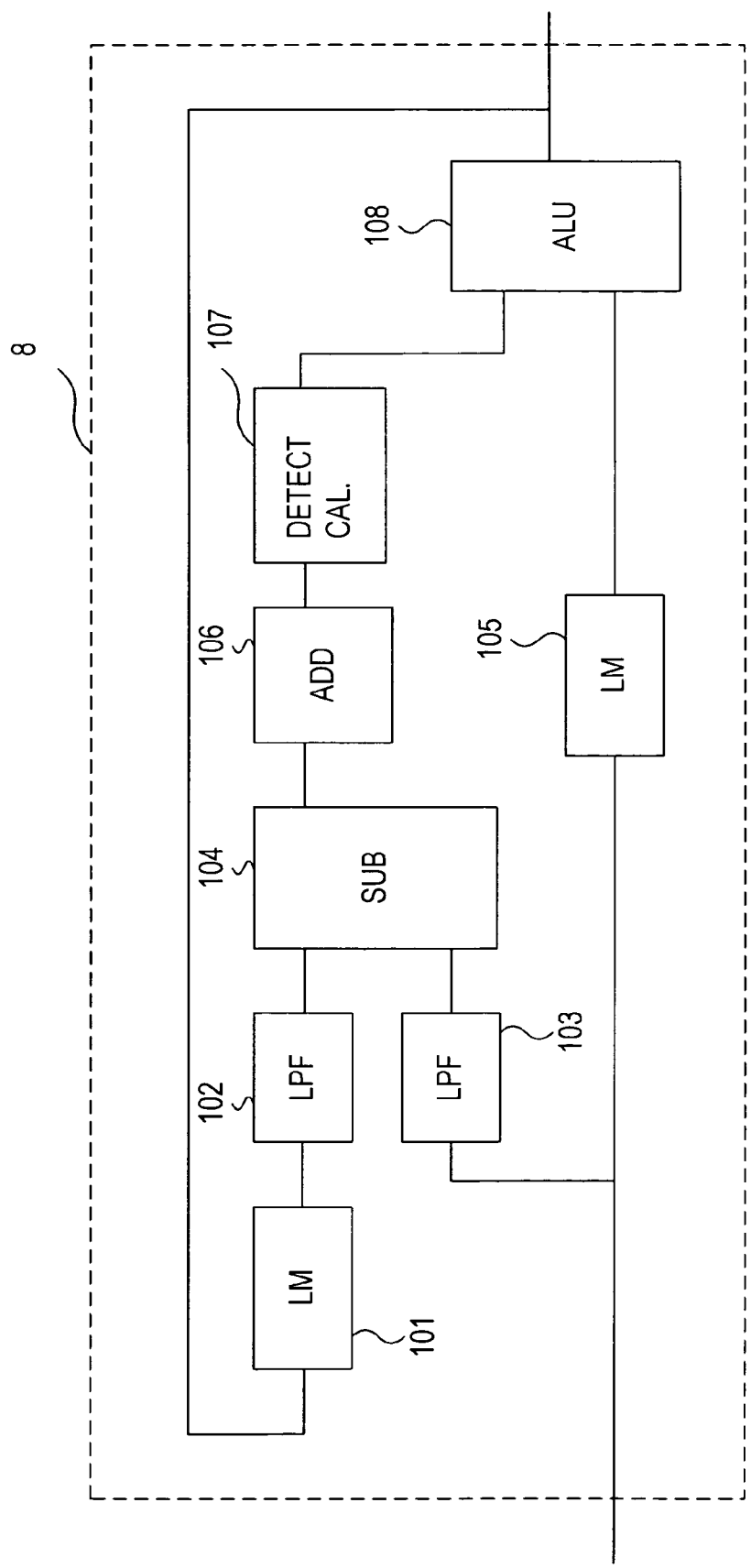
FIG. 2 is a block diagram illustrating the structure of an X-ray diagnostic apparatus according to Embodiment 1 of the present invention.

FIG. 2 is a block diagram illustrating an example of the noise eliminating unit 8, which is provided for eliminating noise included in image data detected by the two-dimensional semiconductor X-ray detector (FP) in accordance with the present invention. Since all components of the X-ray diagnostic apparatus according to Embodiment 1 are known except for the noise eliminating unit 8, the noise eliminating unit 8 will be described in more detail hereinafter. However, although a case will be considered in which subtracting means 104, adding means 106, judging means 107, and calculating means 108 are realized by a program executed in a known information processing unit forming part of the X-ray diagnostic apparatus according to Embodiment 1, these components may be realized by dedicated hardware as well.

The noise eliminating unit 8 according to Embodiment 1 includes: a first line memory 101 for storing image data of one scan line (of one line) that has been output by calculating means 108; a first low pass filter 102 for eliminating high-frequency components of the image data read out from the line memory 101; a second low pass filter 103 for eliminating high-frequency components of X-ray image data for one line that has been output by correcting means (not shown); subtracting means 104 for subtracting a pixel value of image data after correction that has passed through the second low pass filter 103 from a pixel value of image data that has been received from the first line memory 101 through the first low pass filter 102, both pixel values belonging to a common address in a line direction; adding means 106 for sequentially adding the values output by the subtracting means 104, which represents the difference between the pixel value on a predetermined line and a pixel value on a line immediately before the predetermined line; judging means 107 for comparing the above added value (sum) of the difference values for one line with a predetermined value (not shown), so as to judge whether the sum is in a predetermined range; and calculating means 108 for applying a predetermined correction to the image data stored in a second line memory in accordance with the judgment by the judging means 107, and for outputting the corrected data.

Next, the operation of eliminating the line correlation noise using the noise eliminating unit 8 according to Embodiment 1 will be described.

An X-ray beam impinging on a detector FP is converted into an electric signal by the detector FP and is sequentially output to correcting means (not shown) as image data for each scan line. The image data input to the correcting means is first separated into image data of a dark area 401 and image data of an effective area 402, respectively, as shown in FIG. 5. Next, the average value of the image data in the dark area is calculated, this value is subtracted from the image data in the effective area 402 using the average value as data for correction for a line to be corrected, and the image data of the effective area 402 after the above subtraction is sequentially input into the noise eliminating unit 8 according to Embodiment 1.

In the noise eliminating unit, the image data of the effective area 402, after correction, is input to the second low pass filter 103 and also to the second line memory 105. After high-frequency components of the image data input into the second low pass filter 103 are cut off, the image data is input to the subtracting means 104.

Here, if image data input to the subtracting means 104 consists of the first line for one frame, image data consisting of the last line of the immediately preceding frame or an initial value (for example, zero) is stored in the first line memory 101. Therefore, according to Embodiment 1, the calculating means 108 outputs the data that has been input into the second line memory 105 as data that has been subjected to noise elimination. Therefore, the noise is not eliminated from the image data on the first line. However, because the operator of the equipment ordinarily conducts the X-ray fluoroscopy and X-ray radiography while positioning a region of interest (ROI) so that it is located on the center of the display monitor, it is not a problem even if noise is generated on the first line located on the upper edge of the display monitor. Embodiment 1 is constructed so that image data that has been output from the correction means (not shown), and including information of a line representing whether or not this image data represents the first line for one frame, are input to the calculating means 108, and the calculating means 108 judges whether the image data input to the second line memory 105 is to be output as it is, or if it is to be output after eliminating noise therefrom. Accordingly, in Embodiment 1, it is not especially essential whether or not the subtracting means 104, the adding means 106, and/or the judging means 107 operate as predetermined when the input image data relates to the first line for one frame.

Meanwhile, when image data input to the subtracting means 104 is related to the second or subsequent lines of one frame, image data stored on the first line memory 101 represents the line immediately preceding the line input to the noise eliminating unit 8. Accordingly, as shown in FIG. 6, the result 503 of subtracting the image data 502 of the immediately preceding line that has been input to the subtracting means 104 via the first low pass filter 102 from the image data 501 that has been input to the subtracting means 104 via the second low pass filter 103 is obtained for each pixel on an identical address in a line direction and is output by the subtracting means 105. The values of these subtracting results 503 are sequentially added by the adding means 106. Here, according to Embodiment 1, the result of addition (the output of the adding means 106) is constantly output to the judging means 107. Needless to say, the addition result also may be output by the adding means 106 to the judging means 107 only after the addition for one line is finished.

When the addition for one line is finished, it is judged whether or not the sum is in a predetermined range of value (for example, in the range of 5120 to 10240), whereby it is judged whether or not noise is mixed in the line data or not, and the resultant judgment is output to the calculating means 108, as described in connection with the above-mentioned principle. Here, if it is judged that noise is not mixed in the line data, image data for one line, which data has been stored in the second line memory 105, is output as image data that has been subjected to noise elimination via the calculating means 108. At this point, the image data output by the calculating means 108 is sequentially stored in the first line memory 101, and it is also stored in storing means (not shown) for collecting image data.

Meanwhile, if it is judged by the judging means 107 that a noise is mixed in the image data, as described above, after the calculating means 108 calculates a value obtained by averaging the sum acquired by the adding means 106 with an added pixel number, a value obtained by subtracting the average value from the value of image data for each pixel in the second line memory is output as the image data after noise elimination. The image data output by the calculating means 108 is sequentially stored in the first line memory 101 and in the storing means (not shown) for collecting image data.

Subsequently, a noise which has been mixed in the dark area signal and is unable to be removed by the correcting means is eliminated by sequentially repeating the above-described noise eliminating operation at each line.

In this manner, after the image data from which the noise has been eliminated is stored in the storing means (not shown) which is used for holding the X-ray images, as described above, it is also stored in a conventional hard disk device, an optical disk device, a magneto-optical disk device, or the like, which are included in the information processing unit constituting the X-ray diagnostic apparatus according to Embodiment 1. Further, the image processing unit 7 sequentially reads out the image data from the storing means, performs a known image processing, such as conventional edge enhancement and gray scale correction, and outputs the processed image data to the image display unit 9. In the image display unit 9, the image data for one frame is converted into a known input signal format for the display means, such as a television monitor, and an X-ray image is displayed on the surface of the display means. At this time, in the X-ray diagnostic apparatus according to Embodiment 1, an X-ray image, in which the effect of noise mixed in the dark area 401 is corrected, can be displayed.

EMBODIMENT 2

Figure 3:
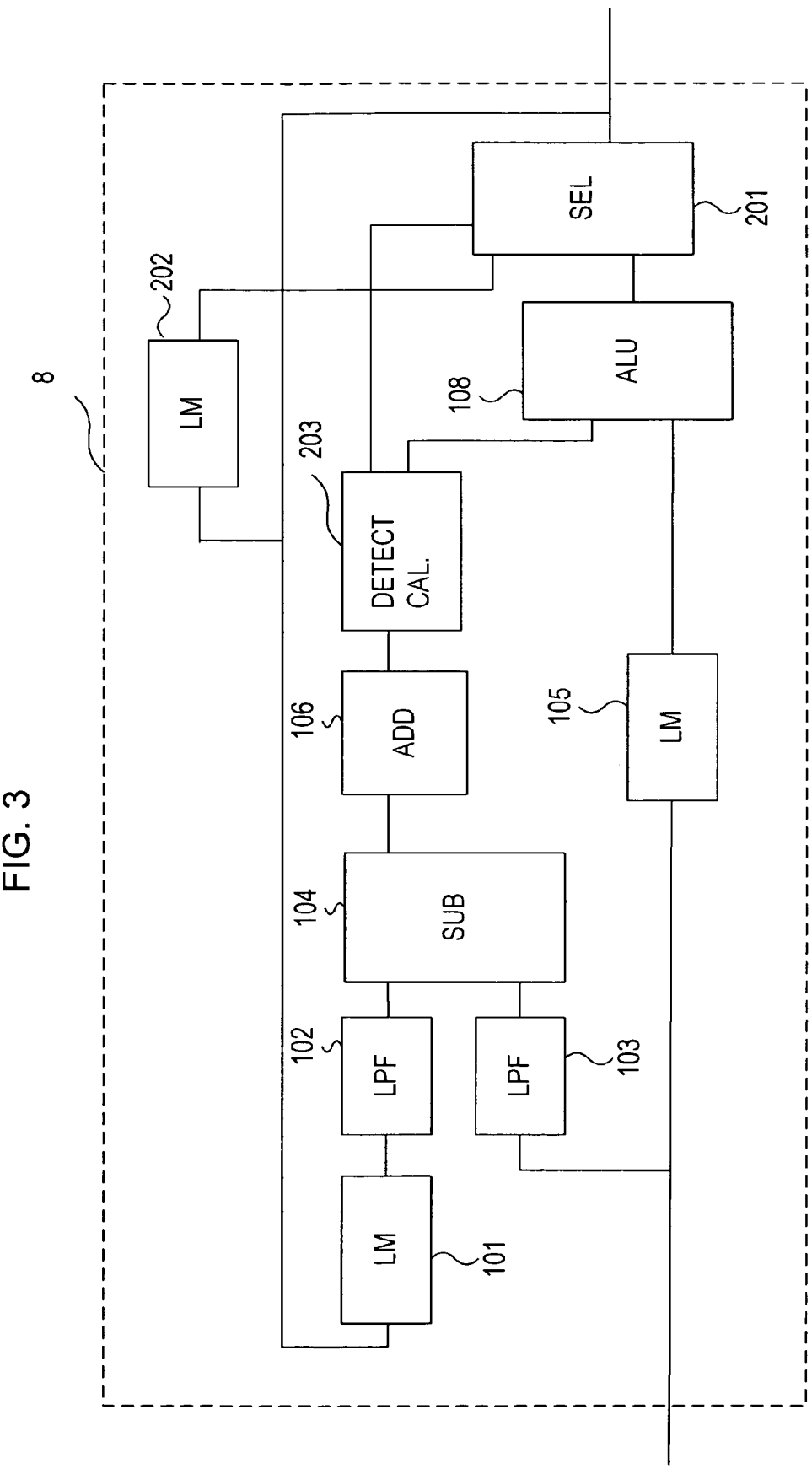
FIG. 3 is a diagram illustrating the structure of an X-ray diagnostic apparatus according to Embodiment 2 of the present invention.

FIG. 3 is a block diagram illustrating another example of the noise eliminating unit 8 for eliminating a noise included in image data detected by the FP in accordance with the present invention. However, because the noise eliminating unit 8 of the X-ray diagnostic apparatus according to Embodiment 2 has the same structure as that of Embodiment 1, except for the selecting means 201, a third line memory 202, and judging means 203, only the selecting means 201, the third line memory 202, and the judging means 203 will be described in detail. Although a case will be considered in which the selecting means 201 and the judging means 203 are realized by a program operating through a conventional information processing unit, it is also possible to realize such features by use of dedicated hardware.

The noise eliminating unit 8 according to Embodiment 2 is constructed to include selecting means 201 for selecting as the output of the noise eliminating means 8 between image data output by the calculating means 108 and image data stored in a third line memory 202. However, the third line memory 202 always stores image data corresponding to the line immediately before the line of which image data has been stored in the second memory 105, in the same manner as in the first line memory 101.

Here, the judging means 203 according to Embodiment 2 has an output function for indicating when a sum output by the adding means 106 exceeds a judgment value (for example, 10240) according to Embodiment 1, in addition to the function of the judging means 107 according to Embodiment 1, as described above. That is, the judging means 203 according to Embodiment 2 sends an output generated by the function of the judging means 107 according to Embodiment 1 to the calculating means 108. If the above sum exceeds the judgment value, the output is sent to the selecting means 201.

Consequently, in the noise eliminating unit 8 according to Embodiment 2, if the value acquired by adding the differences between inputted image data of one line and image data of the immediately preceding line exceeds the judgment value, it is judged that an unremovable noise is mixed in any of the dark area 401 or the effective area 402, and image data on the line where the noise has entered is replaced with that of the immediately preceding line and is output as noise-free image data for the line. Image data to be replaced with a line where a large noise is detected is not limited to image data of the immediately previous line; it may be replaced with image data of the succeeding line, or image data that has been interpolated from image data on the preceding and the succeeding lines, or the image data on still another line.

However, image data output by the selecting means 201 is stored in the storing means (not shown) which is used for holding the X-ray images, and, after that, it is stored on a conventional hard disk device, optical disk, or magneto-optical disk included in the information processing unit that constitutes the X-ray diagnostic apparatus according to Embodiment 2, in the same manner as in the X-ray diagnostic apparatus according to Embodiment 1. Further, the image processing unit 7 sequentially reads out images from the storing means, performs conventional image processing, such as edge enhancement and gray-scale correction, and outputs the processed image data to the image display unit 9. In the image processing unit 9, the image data for one frame is converted into signals in the format of conventional display means, such as a television monitor, and an X-ray image is displayed on the surface of the display means, whereby the same effect as provided in the above-described X-ray diagnostic apparatus according to Embodiment 1 is obtained. At this time, in an ultrasonic diagnostic apparatus according to Embodiment 2, the image data on the line where a large noise is mixed entered is replaced with that of another line or that generated on the basis of image data of another line, whereby an X-ray image having a further improved noise eliminating performance can be collected and displayed.

EMBODIMENT 3

Figure 4:
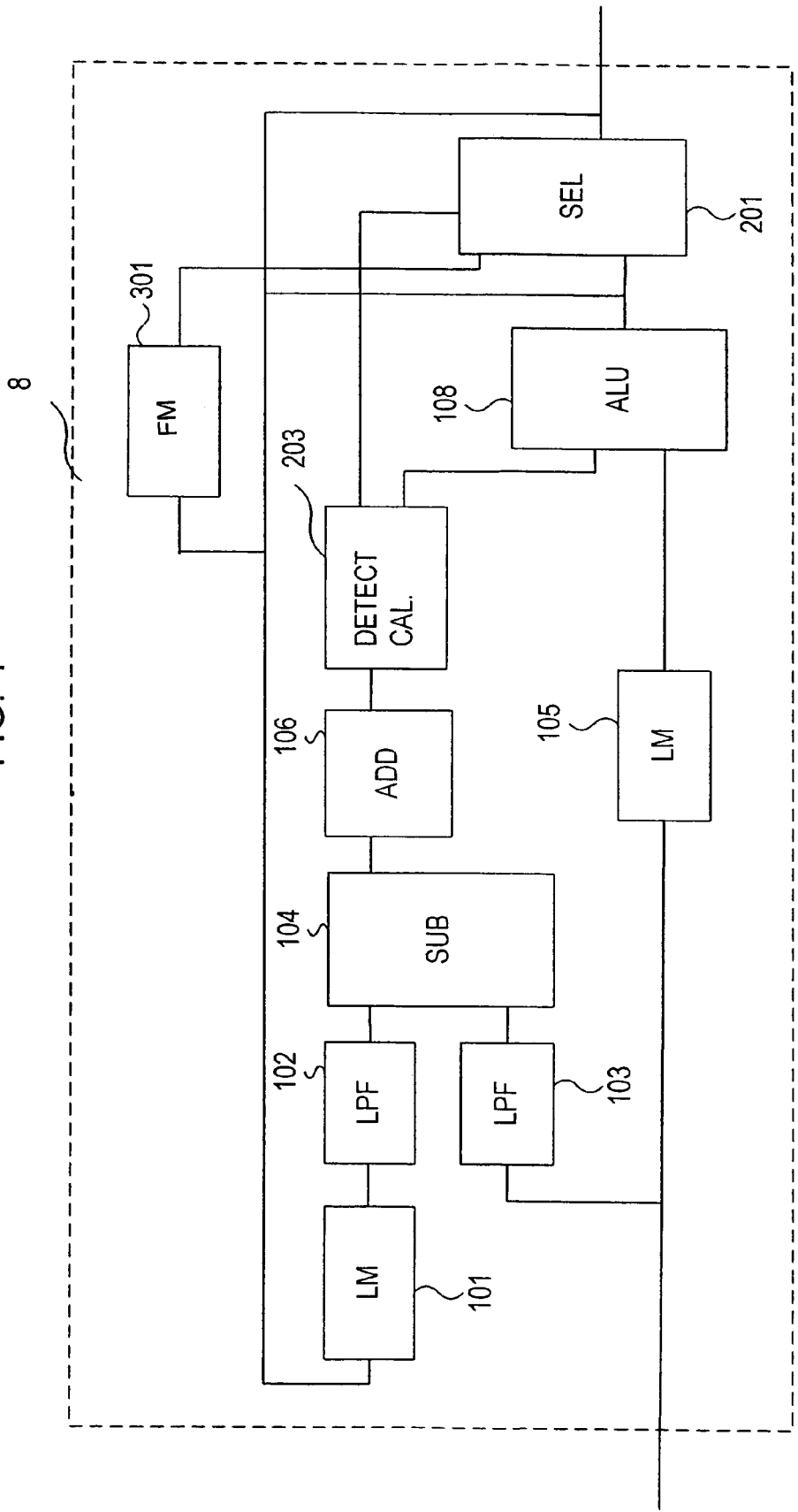
FIG. 4 is a diagram illustrating the structure of an X-ray diagnostic apparatus according to Embodiment 3 of the present invention.

FIG. 4 is a diagram illustrating another example of the noise eliminating means 8 for eliminating noise included in image data detected by the FP in accordance with the present invention. However, because all the components of the noise eliminating unit 8 in the X-ray diagnostic apparatus according to Embodiment 3 are the same as those of the noise eliminating unit 8 according to Embodiment 2, except for a frame memory 301, hereinafter only the frame memory 301 will be described in detail. In the same manner as Embodiment 1, the frame memory 301 can be realized by an external memory included in a conventional information processing unit forming the X-ray diagnostic apparatus according to Embodiment 3.

The frame memory 301 works as a storing means for storing image data of an immediately preceding frame of image data on a line input by the correcting means (not shown). Accordingly, in the noise eliminating unit 8 according to Embodiment 3, if a value that is acquired by adding the differences between the image data of an inputted line and that of a line immediately preceding the inputted line exceeds a judgment value, it is judged that an unremovable noise is mixed in a dark area 401 or an effective area 402, and image data on the line is replaced with that of the immediately preceding frame for one frame. Incidentally, the image data to be replaced with that on a line where a large noise is detected is not limited to the image data on the immediately preceding frame, and it may be image data of the immediately succeeding frame, that interpolated on the basis of the immediately preceding and the immediately succeeding frames, or that of still another frame.

However, although the replacement of the image data according to Embodiment 3 is effective in X-ray fluoroscopy for consecutively collecting image data on a plurality of frames, it is inapplicable when X-ray images are collected one by one, as in X-ray radiography. Therefore, it is possible to constitute an X-ray diagnostic apparatus that is applicable to both X-ray fluoroscopy and X-ray radiography by eliminating noise by use of the noise eliminating unit 8 according to Embodiment 3 during X-ray fluoroscopy and by use of the noise eliminating unit 8 according to Embodiment 1 or 2 during X-ray radiography.

The present invention has been specifically described according to several embodiments; however, the present invention is not limited to the above-described embodiments, but can be modified in various ways without departing from the scope thereof.

What is claimed is:

1. An X-ray diagnostic apparatus comprising: an X-ray tube for irradiating an object to be examined with an X-ray; a two-dimensional X-ray detector for detecting an X-ray passing through the object; image processing means for producing an image signal to display an image of the X-ray signal from the two-dimensional X-ray detector; and image display means for displaying the image, the X-ray diagnostic apparatus further comprising adding means for sequentially adding difference values between a pixel value on a predetermined line of the two-dimensional X-ray detector and a pixel value on a line adjacent to the predetermined line at each pixel so as to obtain an added value; judging means for comparing the added value with a predetermined value to judge if line noise exists; and noise eliminating means for eliminating line noise in accordance with the judgement by the judging means.

2. An X-ray diagnostic apparatus according to claim 1, wherein the noise eliminating means includes subtracting means for performing subtraction between the X-ray signals of the two adjacent lines, and for producing a noise correcting signal from a difference value calculated by the subtracting means.

3. An X-ray diagnostic apparatus according to claim 1, wherein the noise eliminating means includes: subtracting means for subtracting between a value of a pixel on a scan line immediately preceding a first scan line and a value of a pixel on the first scan line of the two-dimensional X-ray detector; an adder for adding difference values calculated by the subtracting means to obtain an added value; and calculating means for calculating an average difference value for each scan line from the added value obtained by the and correcting the pixel value of the first scan line by using the average difference value.

4. An X-ray diagnostic apparatus according to claim 3, wherein the subtracting means performs subtraction in an area where an X-ray is not detected.

5. An X-ray diagnostic apparatus according to claim 3, wherein, when the judging means judges that the line noise exists, the calculating means corrects the pixel value of the first scan line by the average difference value.

6. An X-ray diagnostic apparatus according to claim 3, wherein the calculating means corrects the pixel value of the first scan line by replacing it with a pixel value of the scan line immediately preceding the first scan line.

7. An X-ray diagnostic apparatus according to claim 3, wherein the calculating means corrects a pixel value of the first scan line by replacing it with a value obtained by interpolating pixel value of pixel values of two scan lines adjacent to the first scan line.

8. An X-ray diagnostic apparatus according to claim 3, wherein the calculating means corrects the pixel values of the first scan line by replacing a value of each pixel with that of an identical pixel in the adjacent frame.

9. An X-ray diagnostic apparatus according to claim 3, wherein the calculating means corrects the pixel value of the first scan line by replacing it with a value obtained by interpolating values of two corresponding pixels in sandwiching frames in an identical scan line.

10. An X-ray diagnostic apparatus according to claim 3, wherein pixel values on scan lines of the two-dimensional X-ray detector are repeatedly corrected for each scan line.

11. An X-ray diagnostic apparatus according to claim 1, wherein the judging means judges a line noise mixture in the pixel value of the predetermined line by judging that the added value is in a range where a standard value of the line noise for one pixel is multiplied by a pixel number in one line.

12. An X-ray diagnostic apparatus according to claim 11, wherein, when the judging means judges that a line noise does not exist, the pixel value of the first scan line is not corrected and output as is.

13. An X-ray diagnostic apparatus according to claim 1, wherein the noise eliminating means includes: a first line memory for storing image data of one scan line; a second line memory for storing image data of scan line immediately preceding the one scan line stored in the first line memory; a first low pass filter for removing a high-frequency component of the image data read out from the first line memory; a second low pass filter for removing a high-frequency component of the image data of the preceding scan line; subtracting means for calculating a difference between values of pixel of the image data from the first line memory passing through the low pass filter and of the image data passing through the low pass filter on the same address in line directions; an adder for adding the difference value to the pixel value on a predetermined scan line, the pixel value being an output value from the subtracting means; and calculating means for providing the image data on an adjacent scan line for a predetermined correlation, and for outputting thus-corrected image data as a corrected output.

14. An X-ray diagnostic apparatus according to claim 13, comprising determining means for comparing the difference value with a predetermined standard value, and determining whether or not the difference value is within a range.

15. An X-ray diagnostic apparatus according to claim 14, wherein, when existence of a line noise is determined by the determining means, the calculating means calculates a value by dividing it by the number of pixels to which the added values obtained by the adder are added, and provides the image data of the adjacent scan line with a predetermined correction and outputs the thus-corrected value.

16. An X-ray diagnostic apparatus according to claim 14, wherein, when it is determined that there is no line noise by the determining means, the image data of the adjacent scan line is output as the image data via the calculating means.

17. An X-ray diagnostic apparatus according to claim 13, wherein the calculating means replaces the image data on the first scan line with the image data on the scan line adjacent to the first scan line to correct the image data.

18. An X-ray diagnostic apparatus according to claim 13, wherein the calculating means interpolates two scan lines adjacent to the first scan line to apply to the image data on the first scan line.

19. An X-ray diagnostic apparatus according to claim 13, wherein the calculating means replaces the image data on the first scan line with the image data on an identical line in a frame adjacent to the first scan line to correct the image.

20. An X-ray diagnostic apparatus according to claim 13, wherein the calculating means replaces a pixel value on the first scan line with an interpolated value of two image values on a scan line at a line which is the same as that of the first scan line in frames adjacent to the first scan line.

21. An X-ray diagnostic apparatus according to claim 13, wherein pixel values on scan lines of the two-dimensional X-ray detector are repeatedly corrected for each scan line.

22. An X-ray diagnostic apparatus according to claim 1, wherein the noise eliminating means includes means for determining whether or not a correction of a pixel value on a scan line is necessary, in accordance with the sizes of value of pixels on a scan line and sizes of value of predetermined pixels in a non-detecting area where the X-ray beam is impinged in the two-dimensional X-ray detector; and means for correcting at least the pixel values on the scan line in a detecting area where the X-ray beam is impinged with the values of peripheral pixels when necessity of correction is resultantly determined.

23. An X-ray diagnostic apparatus according to claim 1, wherein the noise eliminating means includes means for determining whether or not a correction of a pixel value on a scan line is necessary depending on sizes of value of pixels on a scan line and sizes of value of pixels in a non-detection area in the two-dimensional X-ray detector where an X-ray beam is not impinged; and means for correcting at least the pixel values on a scan line in a detection area with the pixel values of the scan line in sequentially collected X-ray images.

24. An X-ray diagnostic apparatus according to claim 1, wherein all of the difference values of one line are summed.

* * * * *